United States Patent [19]

Bargeron et al.

[11] 4,251,459
[45] Feb. 17, 1981

[54] PREPARATION OF N-(2-MERCAPTOETHYL)ALKANAMIDES

[75] Inventors: Kim G. Bargeron; Thad S. Hormel; David K. Winegardner; Bruce G. Lovelace, all of Midland, Mich.

[73] Assignee: The Dow Chemical Company, Midland, Mich.

[21] Appl. No.: 56,474

[22] Filed: Jul. 11, 1979

[51] Int. Cl.³ .................... C07C 102/00; C07C 85/00
[52] U.S. Cl. ..................................... 564/215; 564/78; 564/154; 564/219; 564/224
[58] Field of Search ..................................... 260/561 S

[56] References Cited

U.S. PATENT DOCUMENTS

| 4,086,273 | 4/1978 | Berazosky et al. | 260/561 S |
| 4,086,274 | 4/1978 | Kaiser et al. | 260/561 S |

Primary Examiner—Arthur P. Demers
Attorney, Agent, or Firm—Michael L. Glenn

[57] ABSTRACT

The title compounds are prepared by the reaction of a 2-alkyl-2-oxazoline with hydrogen sulfide in a continuous process wherein both reactants are maintained in the liquid phase throughout the reaction by the use of superatmospheric pressure. This continuous process reduces the reaction time substantially compared to prior art process and also reduces the quantity of by-products.

6 Claims, No Drawings

PREPARATION OF N-(2-MERCAPTOETHYL)ALKANAMIDES

BACKGROUND OF THE INVENTION

This invention relates to an improved process for preparing N-(2-mercaptoethyl)alkanamide.

Kaiser and Owen teach in U.S. Pat. No. 4,086,274 that N-(2-mercaptoethyl)alkanamides are prepared by the reaction of a 2-alkyl-2-oxazoline with hydrogen sulfide. Substantially any reaction temperature from about 20° C. to about 200° C. and autogenous or superatmospheric pressure are recited to be suitable operating conditions. In Example 1 in the patent, a reaction time of more than 5 hours is utilized in a batchwise process to effect an 85.1 percent yield of the desired amide based on the oxazoline reactant at a reaction temperature of 100° C.–110° C. and a maximum pressure of 320 pounds per square inch gauge (psig).

SUMMARY OF THE INVENTION

It has now been discovered that the process for preparing an N-(2-mercaptoethyl)alkanamide represented by the formula

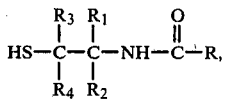

wherein R is alkyl and $R_1$–$R_4$ are each independently hydrogen, lower alkyl ($C_1$–$C_6$), hydroxy-substituted lower alkyl or phenyl is improved by reacting hydrogen sulfide with a 2-alkyl-2-oxazoline in a molar ratio from at least about 1.0 to about 1.2 in a continuous process wherein both the reactants are maintained in the liquid phase throughout the reaction by the application of superatmospheric pressure.

DETAILED DESCRIPTION OF THE INVENTION

The 2-alkyl-2-oxazoline reactant corresponds to the formula

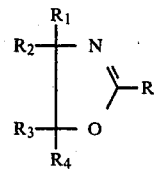

in which R and $R_1$–$R_4$ have the aforesaid meanings. Preferably R is an alkyl group of from 1 to about 18 carbon atoms and most preferably R is methyl or ethyl. Preferably, $R_1$–$R_4$ are each independently hydrogen, methyl, ethyl or hydroxymethyl and more preferably $R_3$ and $R_4$ are each hydrogen. Most preferably, $R_1$–$R_4$ are each hydrogen. The 2-oxazolines used herein can be prepared by conventional processes, which are well documented in the literature.

Hydrogen sulfide is also a well-known compound. It is a colorless gas at atmospheric pressure at the reaction temperatures utilized in the disclosed improved process. In order to maintain it in the necessary liquid phase during the instant reaction, superatmospheric pressures must be employed.

The 2-alkyl-2-oxazoline and the hydrogen sulfide must be intimately and homogenously mixed in the proper mole ratios prior to substantial reaction in order to minimize the formation of by-products. It is desirable that no diluent be employed. The oxygen present in this reaction mixture is desirably minimal, as it will react with the product. Conveniently, the reactants are mixed at a temperature in the range from about 10° C. to about 50° C. in a mole ratio in the range from greater than about 1.0 to about 1.2, preferably about 1.05 to about 1.15, of the hydrogen sulfide with respect to the 2-oxazoline reactant. It is preferred that liquid hydrogen sulfide is mixed with liquid 2-alkyl-2-oxazoline. However, it is operable, but less desirable, to mix gaseous hydrogen sulfide with the liquid oxazoline and then to liquefy the mixture with superatmospheric pressure, so long as substantial reaction does not occur. The use of more than a 20 percent mole excess of hydrogen sulfide makes the maintenance of an entirely liquid reaction phase extremely difficult. The use of less than a 10 percent mole excess of hydrogen sulfide may result in the clogging of the outlets of the reaction vessel with by-products, especially at reaction temperatures above 160° C.

After the reactants have been thoroughly premixed, they are introduced into the reaction vessel and heated to the desired reaction temperature with suitable pressure to maintain a liquid phase. The reaction vessel can be a simple pipe connected to suitable valves and pumps to maintain the reaction pressure and suitable means to control the reaction temperature. The reaction temperature should be in the range from about 100° C. to about 180° C., preferably about 135° C. to about 165° C. The minimum reaction pressure necessary to maintain a liquid phase in the reaction mixture is typically at least about 550 to 600 psig, with higher pressures in this range being necessary at higher reaction temperatures. The reaction pressure can operably be much greater than these minimum values, but pressures less than 900 psig are generally preferred because of the relatively greater cost of equipment operable at higher pressures.

The reaction time necessary for complete conversion of the 2-alkyl-2-oxazoline varies with reaction temperature. About 40 minutes are necessary at 100° C. to effect complete conversion, whereas only about 5 minutes are required at 135° C. The residence time in the reaction vessel can be varied to match the minimum reaction time by varying the flow rate of the reactants or the length of said vessel.

The following examples further illustrate the invention. Unless otherwise indicated all parts and percentages are by weight.

EXAMPLES 1–6

The 2-ethyl-2-oxazoline reactant, containing about 0.2 percent water, and the liquid hydrogen sulfide are charged to separate reactant reservoirs. The 2-ethyl-2-oxazoline feed is purged with nitrogen to remove any dissolved oxygen. The reactants are pumped through separate stainless steel feed lines at rates at 63.9 and 169 grams per hour for the hydrogen sulfide and 2-ethyl-2-oxazoline, respectively. These feed lines are merged by means of a "Y"-connector, the resulting turbulence provides a homogenous reaction mixture containing 1.1 moles of $H_2S$ for each mole of 2-ethyl-2-oxazoline.

The reaction mixture is fed directly into a 23-foot long coil of stainless steel tubing one-eighth inch in diameter maintained at a desired temperature by immersion in a heat bath. The high surface area to volume ratio ensures good heat transfer. The residence time in the reaction vessel is nominally 5.4 minutes. A back-pressure control valve following the coil reaction vessel maintains a pressure of about 830–840 psig upstream. After passing through the coil reaction vessel, the product stream is depressurized, collected and analyzed by standard iodide/iodate titration and conventional liquid chromatographic techniques to determine the yield of the desired product. The above-described procedure is repeated at six different reaction temperatures and the weight percent N-(2-mercaptoethyl)propionamide (MEP) along with a thiocarboxamide (TCA) and a diamide mercaptan (DAM) by-product are tabulated for each run in Table I.

TABLE I

| Example | Temperature (°C.) | Weight Percent | | |
|---|---|---|---|---|
| | | MEP | TCA | DAM |
| 1 | 101 | 60 | 15.0 | 2.2 |
| 2 | 115 | 83 | 8.8 | 3.8 |
| 3 | 130 | 86 | 6.5 | 5.3 |
| 4 | 144 | 89 | 3.5 | 6.3 |
| 5 | 149 | 88 | 3.0 | 6.6 |
| 6 | 158 | 90 | 2.4 | 7.6 |

As can be seen from the data presented in Table I, the weight percent of the desired product produced is at least 83 percent in all the runs except the first. A residence time of 5.4 minutes is found to be insufficient at a reaction temperature of 101° C. as 22 percent of the crude product is the 2-ethyl-2-oxazoline reactant. The by-product which predominates is the thiocarboxamide ($C_2H_5CSNC_2H_4OH$) at the lower reaction temperatures and the diamide mercaptan (($C_2H_5CONHC_2H_4)_2S$) at the higher reaction temperatures.

COMPARATIVE EXPERIMENT

2-Ethyl-2-oxazoline is charged to a 50-gallon glass-lined reactor under a nitrogen atmosphere at a temperature of about 50° C. Gaseous hydrogen sulfide is charged to the reactor over a 2-hour period at a temperature of 50° C., so as to effect an ultimate mole ratio of hydrogen sulfide to 2-ethyl-2-oxazoline of about 1.1. Pressures of up to 150 psig are reached during this addition step. A sample of this reaction mixture is analyzed by conventional techniques and is found to contain 75 percent N-(2-mercaptoethyl)propionamide, 22 percent of the thiocarboxamide by-product and 3 percent of the diamide mercaptan.

The reactor is heated to 150° C. for 5 hours to reduce the presence of the thiocarboxamide by-product in the crude product. The resulting product when analyzed by conventional techniques is found to consist of 83 percent N-(2-mercaptoethyl)propionamide, 0.5 percent of the thiocarboxamide and 10.0 percent of the diamide mercaptan.

It is clear from the foregoing comparative experiment, that the disclosed continuous, liquid-phase process is surprisingly much faster and produces better yields than the prior art batchwise process.

What is claimed is:

1. In a process for preparing an N-(2-mercaptoethyl)alkanamide represented by the formula

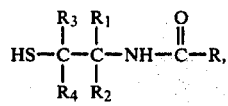

wherein R is alkyl and $R_1$–$R_4$ are each independently hydrogen, lower alkyl, hydroxy-substituted lower alkyl or phenyl by reacting a 2-alkyl-2-oxazoline with hydrogen sulfide under essentially anhydrous conditions, the improvement comprising reacting in a continuous process, the hydrogen sulfide with the 2-alkyl-2-oxazoline in a molar ratio from at least about 1.0 to about 1.2 moles of hydrogen sulfide per mole of the oxazoline, wherein both the reactants are maintained in the liquid phase throughout the reaction by the application of superatmospheric pressure and the reaction temperature is in the range from about 100° to about 185° C.

2. The process as described in claim 1 wherein the 2-alkyl-2-oxazoline and the hydrogen sulfide reactant are premixed in the specified ratio prior to the occurrence of substantial reaction.

3. The process as described in claim 2 wherein the reaction temperature is in the range from about 135° C. to about 165° C.

4. The process as described in claim 3 wherein the 2-alkyl-2-oxazoline is 2-methyl-2-oxazoline or 2-ethyl-2-oxazoline.

5. The process as described in claim 4 wherein the reaction pressure is in the range from about 550 to 900 psig.

6. The process as described in claim 2 wherein the reaction temperature is in the range from about 115° C. to about 160° C.

* * * * *